United States Patent [19]

Ohno

[11] Patent Number: 4,600,146

[45] Date of Patent: Jul. 15, 1986

[54] SUSTAINEDLY VAPOR-RELEASING BODY HAVING EXCELLENT SHAPE-RETAINABILITY

[75] Inventor: Shigeru Ohno, Kanagawa, Japan

[73] Assignee: Shin-Etsu Chemical Co., Ltd., Tokyo, Japan

[21] Appl. No.: 352,759

[22] Filed: Feb. 26, 1982

[30] Foreign Application Priority Data

Mar. 24, 1981 [JP] Japan .................................. 56-42879

[51] Int. Cl.$^4$ .............................................. A61L 9/04
[52] U.S. Cl. ........................................ 239/6; 138/103; 138/115; 138/DIG. 8; 239/53
[58] Field of Search .................................... 239/53–56, 239/57, 44, 6; 138/103, 111, 115, 122, 129, 134, DIG. 8

[56] References Cited

U.S. PATENT DOCUMENTS

| | | | |
|---|---|---|---|
| 2,139,888 | 12/1938 | Fausek et al. | 138/115 |
| 2,238,476 | 4/1941 | Monteith | 239/53 |
| 2,704,556 | 3/1955 | Blish | 138/DIG. 8 |
| 2,722,237 | 11/1955 | Rosel | 138/103 X |
| 2,998,028 | 8/1961 | Rohde | 138/DIG. 8 X |
| 3,770,199 | 11/1973 | Hoek et al. | 239/54 |
| 4,017,030 | 4/1977 | Coplan et al. | 239/53 X |

Primary Examiner—Joseph F. Peters, Jr.
Assistant Examiner—Daniel R. Edelbrock
Attorney, Agent, or Firm—Toren, McGeady, Stanger, Goldberg & Kiel

[57] ABSTRACT

The invention provides a novel integrated body of an elongated form capable of sustainedly releasing vapor of a vaporizable substance contained in the body into the atmosphere, such as an aromatic compound, pesticide, fungicide and a sex pheromone as a means for the control of a pest. The inventive sustainedly vapor-releasing integrated body is very advantageous in the high efficiency of shaping into desired configuration and setting or installation in the field in large numbers by virtue of the good shape-retainability as a result of the integrated structure composed of a capillary tubing of a polymeric material filled with the vaporizable substance and a metal wire with plastic deformability and a sufficiently large cross section and integrated side-by-side with the capillary tubing to retain the latter in the compulsorily deformed disposition. The inventive integrated bodies are suitable for mass production in a relatively simple process.

10 Claims, 9 Drawing Figures

SUSTAINEDLY VAPOR-RELEASING BODY HAVING EXCELLENT SHAPE-RETAINABILITY

BACKGROUND OF THE INVENTION

The present invention relates to a sustainedly vapor-releasing body, which is suitable for mass production, to emit the active vapor of a vaporizable substance contained therein over a long period of time or, more particularly, to a sustainedly vapor-releasing body formed of a capillarly tubing containing the vaporizable substance exhibiting an activity in the vapor phase and having excellent shape-retainability to retain its configuration as bent or deformed without heating so that it can very easily and conveniently be installed and kept or settled stably at any desired place where the activity of the released vapor should be exhibited consequently resulting in the full accomplishment of the object of using such a vapor-releasing body over a long period of time and in the full utilization of the activity of the vaporizable substance.

In recent years, there is a great demand to develop an efficient and convenient means to sustainedly and continuously emit vapors of certain vaporizable substances utilized in the vapor form, which include aromatic compounds, pesticides, bactericides, fungicides, sex pheromones of pests and the like distinctly effective even when present in the air in a trace concentration, into the atmosphere in an extremely low concentration.

Suitable for such a purpose of sustainedly vapor-releasing bodies are the so-called microcapsules, for example, disclosed in the specifications of the U.S. Pat. Nos. 3,539,465 and 3,577,515 according to which the vaporizable substance is contained in the microcapsules and emitted through the very thin walls of the microcapsules at a sustained rate. Microcapsules used for such a sustainedly vapor-releasing purpose are, however, disadvantageous in several aspects. For example, the process of microencapsulation costs very high and considerable amounts of the vaporizable substance are lost during the process of microencapsulation so that the products are necessarily very expensive. In addition, due to the fine particulate form of the microcapsules, it is rather a difficult matter to install the sustainedly vapor-releasing body at a desired place where the activity of the vaporizable substance should be exhibited with lastingness over a long period of months or longer notwithstanding the essential necessity in the practice of such lasting installation to fully accomplish the object of sustained vapor releasing. Therefore, microcapsules have not yet acquired very wide prevalence as a form of the sustainedly vapor-releasing body of the above described type.

An alternative form of the sustainedly vapor-releasing body is described in Japanese Patent Kokai No. 52-55969 according to which the vaporizable substance is contained in a hollow fiber with a sealed end and the vapor of the vaporizable substance is emitted gradually through the other open end of the hollow fiber. The process of preparing such a sustainedly vapor-releasing body is simpler with smaller loss of the vaporizable substance in the course of filling the hollow fiber than in the above mentioned method of microencapsulation resulting in less expensiveness of the products so that the sustainedly vapor-releasing bodies of this form are under practical use to some extent.

One of the serious problems in this form of the sustainedly vapor-releasing bodies is again in the stable installation of the bodies at a desired place where the activity of the vaporizable substance should be exhibited over a long period of time. In order to solve this problem, the use of an adhesive is suggested such that the hollow fiber is coated with an adhesive on at least a part of the outer surface thereof and adhesively bonded to the desired place or to the surface of a second body to which the sustainedly vapor-releasing body is to be bonded. Such a method of using an adhesive is very unsatisfactory from the practical standpoint, especially, when the sustainedly vapor-releasing bodies are to be installed on a living plant of the field such as farms and forests by use of an pesticide, fungicide or sex pheromone as the vaporizable substance which is effective only when the vapor thereof is emitted around the living plant since it is almost impossible to obtain lasting adhesive bonding of a foreign body on to the surface of a living plant without imparting any damages or adverse effects to the plant.

As a remedy for the above described difficulty in the use of an adhesive as a means for the installation of a sustainedly vapor-releasing body of the hollow fiber or capillary tubing type, there is also proposed the use of a thread, string or wire which is connected to the fiber or capillary tubing at one end and the other end thereof is fastened by tying or hanging to plants. Although this method is surely effective in obtaining stability of the installation of the sustainedly vapor-releasing body over a long period of time without imparting damages to the body of the plant, there is a fatal problem in this method when applied to a large-scale field work since the work of connecting the thread, string or wire with the fiber or capillary tubing can be undertaken only by handworks and is so much time-consuming that the applicability of this method is limited only to small-scale research works or testing purposes with no promising possibility of wide applicability to the large-scale field works.

SUMMARY OF THE INVENTION

It is therefore an object of the present invention to provide a novel and improved sustainedly vapor-releasing body of a capillary tubing type which can be manufactured readily in large numbers by a means suitable for mass production and capable of being installed at any desired place in stable setting where the activity of the vaporizable substance contained therein should be exhibited with lastingness over a long period of time with least time or labor consumed for the installation thereof.

Thus, the most characteristic feature of the inventive sustainedly vapor-releasing body is the shape-retainability of the capillary tubing to retain its configuration as bent or deformed.

The sustainedly vapor-releasing body of the invention having the above mentioned characteristic comprises (a) a capillary tubing having flexibility made of a polymeric material, (b) a metal wire having plastic deformability to retain a deformed configuration and integrated with the capillary tubing in a side-by-side manner along the longitudinal direction thereof, and (c) a vaporizable substance filling the pore of the capillary tubing, which is capable of vaporizing through the walls of the capillary tubing and exhibiting an activity in the vapor phase.

DETAILED DESCRIPTION OF THE PREFERRED EMBODIMENTS

Figure 1:
FIG. 1 is a perspective view of a side-by-side integrated body of a capillary tubing and a metal wire.

As is mentioned above, the essential components comprised in the inventive sustainedly vapor-releasing body are a capillary tubing made of a polymeric material, a metal wire integrated side-by-side with the capillary tubing and a vaporizable substance filling the pore of the capillary tubing. The polymeric material suitable for the capillary tubing is preferably a thermoplastic polymer exemplified by, for example, polyolefins, polyacrylic resins, polymethacrylic resins, polyamide resins, polyester resins, cellulose derivatives, organopolysiloxanes and the like. They are used as such or with admixture of suitable amounts of plasticizers, lubricants, heat stabilizers and other conventional additives provided that the moldability of the polymeric composition is not unduly decreased by a known shaping means such as extrusion molding and the like. According to the particular application of the sustainedly vapor-releasing body of the invention, it is sometimes advisable that the polymeric composition for the capillary tubing contains a coloring agent and/or ultraviolet absorber in addition to the above mentioned additives. When the polymeric material is a rubbery elastomer, the composition contains a crosslinking agent and the polymeric material is, after shaping into a tubular form, crosslinked by heating or the like means to be imparted with a three-dimensional structure so that the mechanical strengths or physical and chemical properties of the capillary tubing may be improved.

The dimensions of the capillary tubing are not particularly limitative and should be determined in consideration of several conditions in the application of the sustainedly vapor releasing body. For example, the inner diameter of the capillary tubing may range from about 0.2 mm to about 20 mm and the wall thickness or the tubing may also range from 0.1 mm to 5 mm according to need. Capillary tubings having smaller inner diameter than above are molded with considerable difficulties and the vaporizable substance can hardly be introduced into such a fine pore so that disadvantages from the practical standpoint are unavoidable.

On the other hand, capillary tubings or, rather, plastic tubes having an inner diameter larger than above and capable of containing a large volume of the vaporizable substance are in most cases useless, especially, when the vaporizable substance is a compound having a chemical structure susceptible to the influences of the atmospheric oxygen, moisture, light and the like environmental conditions such as the double bonds, triple bonds, hydroxy groups, aldehyde groups, carbonyl groups and epoxy groups as is likely the case in the active vaporizable substance to be used in the present invention since the vaporizable substance contained in excess of the amount sufficient for a long-term service of one year or longer may be chemically denaturated leading just to the loss of the substance.

Besides the kind of the polymeric material, the wall thickness of the capillary tubing is another important parameter greatly influencing the rate of vaporization of the vaporizable substance through the walls so that the wall thickness should be determined in consideration of the permeability of the substance and the desired concentration of the vapor in the atmosphere. Generally speaking, difficulties are remarkably increased in molding of capillary tubings having a wall thickness smaller than 0.1 mm and capillary tubings with such an extremely thin wall are unsatisfactory due to the collapse or burst of the tubing readily taking place.

On the other hand, a capillary tubing having a wall thickness larger than 5 mm is too rigid and no advantages can be expected excepting the extreme limitation on the rate of emission of the vapor of the vaporizable substance by the diffusion through the wall. In this regard, it is noted that no additional effect is obtained by increasing the wall thickness over 5 mm resulting only in the economical disadvantages and inconvenience in the use of the inventive vapor-releasing body.

The length of the capillary tubing is also not a limiting parameter of the inventive sustainedly vapor-releasing body, which is usually prepared by cutting a continuous-length tubing in a suitable unit length either before or after integration with the metal wire and/or filling of the capillary pore with the vaporizable substance. As a criterion, the inventive sustainedly vapor-releasing body should have a length of at least three times of the outer diameter thereof since shorter bodies are inadequate to the object of the present invention because of the difficulty in the installation thereof by bending or winding around something else at a desired place.

The metal wire to be integrated with the above described capillary tubing of a polymeric material is made of a metal such as aluminum, copper, well-annealed iron or steel, lead, solder alloys, tin and the like. An essential requirement for the metal wire is that the wire is sufficiently plastically deformable and exhibits almost no restorability from the deformed configuration by the resilience when it is once deformed by bending or winding. Accordingly, for example, so-called piano wires as a type of steel wires are not suitable as the metal wire in the present invention due to the particularly enhanced resilience. In short, the metal wire should be readily deformed by hand and retain the deformed configuration as such when the outer force is released.

The cross-sectional size, e.g. diameter, of the metal wire is not particularly limitative provided, when the metal wire is bent or wound together with the capillary tubing with which it is integrated, that it can withstand the elastic resilience of the capillary tubing to restore its undeformed configuration and compulsorily keep the capillary tubing in its deformed state. Metal wires with an excessively large cross section may cause some inconvenience in handling in addition to the economical disadvantage. Flat wires, i.e. wires having a flat cross section, are also suitable for the purpose besides the ordinary wires with circular cross section.

The length of the metal wire to be integrated side-by-side with the capillary tubing should be sufficient to ensure the compulsorily retained deformation of the capillary tubing in the above mentioned meaning so that it can be somewhat longer or shorter than the capillary tubing. As is understood from the following description of the procedure for the preparation of an integrated body of the capillary tubing and the metal wire, however, it is usual that they have substantially the same length since it is the most efficient procedure for the mass production of the inventive vapor-releasing bodies that a capillary tubing of a polymeric material of continuous length is first integrated with the metal wire also in continuous length into an integrated body of continuous length which is subsequently cut into desired unit lengths.

The metal wire to be integrated with the capillary tubing of a polymeric material may be either the wire per se with the bare metal surface exposed or covered with a suitable polymeric material, which may be the same as or different from the polymeric material of the capillary tubing, as in insulated electric wires. It is of course that the surface of the metal wire should be sufficiently cleaned before integration with the capillary tubing in order to ensure good and reliable adhesive bonding between them. For example, machine oils used in the fabrication of the metal wire and adhering thereto must be removed, for example, by use of a solvent. Alternatively, use of a primer is sometimes effective in enhancing the adhesive bonding therebetween.

A further essential component in the inventive sustainedly vapor-releasing body is, of course, a vaporizable substance filling the pore of the capillary tubing. The vaporizable substance may be either liquid or solid at room temperature but should be capable of diffusing through the walls of the capillary tubing in the form of either liquid or vapor and being emitted into the atmosphere as a vapor to exhibit certain activity there. The activity expected of the vapor of the vaporizable substance is, though not limited thereto, mostly physiological so that the vaporizable substance is an aromatic compound, pesticide, fungicide, and bactericide as well as a so-called sex pheromone of a pest which attracts males of the pest even with a trace concentration of the vapor in the air hopefully to provide a promising means for the control of the pests. The vaporizable substance must be inert to the polymeric material of the capillary tubing but diffusible through the wall thereof. It is optional that the vaporizable substance is diluted with a suitable diluent if necessary to control the rate of vapor releasing.

The construction of the inventive sustainedly vapor-releasing body is now described in further detail with reference to the accompanying drawing.

The simplest way of the integration of the capillary tubing made of a polymeric material and the metal wire is illustrated in FIG. 1 by a perspective view of the integrated body, in which the metal wire 2 is directly bonded side-by-side to the outer surface of the capillary tubing 1. The adhesive bonding between them is obtained either by the melting of the surface of the capillary tubing or by the use of a suitable adhesive according to the particular combination of the polymeric material of the tubing 1 and the metal of the wire 2, diameters of them, wall thickness of the capillary tubing 1 and other parameters. As is shown in the figure, the end surfaces of the capillary tubing 1 and the metal wire 2 are flush with each other but this is a consequence of the manufacturing process described below and not particularly limitative.

Figure 2A:
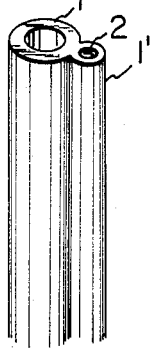
FIG. 2a is a perspective view of a side-by-side integrated body of a capillary tubing and a metal wire with a covering layer.
Figure 2B:
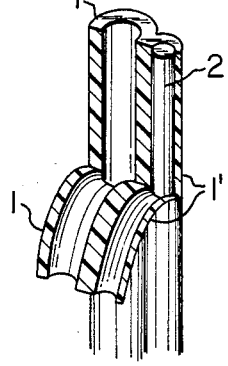
FIG. 2b is a perspective view of the integrated body of FIG. 2a partially cut open.

In place of the bare metal wire 2 used in the integrated body shown in FIG. 1, it is possible to use a metal wire 2 covered in advance with a layer 1' of a polymeric material which is bonded to the outer surface of the capillary tubing 1 side-by-side as is shown by a perspective view in FIG. 2a. When the polymeric materials for the capillary tubing 1 and the covering layer 1' on the metal wire 2 are of one and the same type, adhesive bonding of them by melting together can give very good and reliable integration of the capillary tubing 1 and the metal wire 2. The thickness of the covering layer 1' on the metal wire 2 can be as small as possible provided reliable bonding by melting together is obtained. FIG. 2b illustrates such a well integrated structure of the capillary tubing 1 and the covering layer 1' on the metal wire 2 shown in the cross section obtained by partial cutting and peeling of the capillary tubing 1 and the covering layer 1' made of the same polymeric material.

Figure 3:
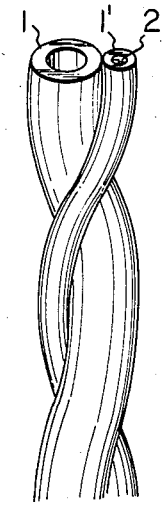
FIG. 3 is a perspective view of an integrated body by intertwisting of a capillary tubing and a metal wire.

Instead of adhesively bonding the capillary tubing 1 and the metal wire 2, uncovered or covered with the covering layer 1', it is an alternative way of integrating a capillary tubing 1 and a metal wire 2 that they are intertwisted with each other as is shown in FIG. 3. This method is sometimes very advantageous since intertwisting of two elongated bodies can be performed by a mechanical means alone without the use of an adhesive or application of heat to obtain adhesive bonding although it may be preferable that the capillary tubing 1 and the metal wire 2 or the covering layer 1' on the metal wire 2 in the thus intertwisted body are adhesively bonded at portions at certain intervals by use of an adhesive or heat in order to prevent loosening or untwisting of them apart.

Figure 4:
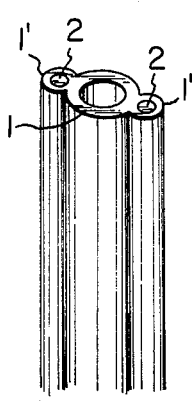
FIG. 4 is a perspective view of a side-by-side integrated body with two metal wires bonded to a single capillary tubing.
Figure 5:
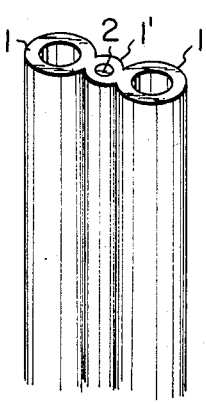
FIG. 5 is a perspective view of a side-by-side integrated body having two capillary tubings bonded together with a single metal wire.

In the above described embodiments, the capillary tubing 1 and the metal wire 2 are integrated together one to one in number. It is of course optional that the capillary tubing 1 and/or the metal wire 2 are used in plurality of two or more to form a single integrated body. FIG. 4 illustrates a perspective view of an example in which a capillary tubing 1 is bonded side-by-side to two metal wires 2 each covered with a covering layer 1' on the radially opposite sides of the capillary tubing 1. Alternatively, a plural number of the capillary tubings 1 can be bonded together side-by-side with a single metal wire 2 as is shown in FIG. 5 by a perspective view. An advantage is obtained with such an integrated body having two or more capillary tubings 1 that each of the capillary tubings 1 contains a different kind of the vaporizable substance from those contained in the other capillary tubings so that a composite effect is readily obtained in the vapor phase by the different kinds of the vaporizable substances, especially, when these vaporizable substances cannot be mixed together in advance due to the problem of stability in the mixed state. It is of course optional that one of the capillary tubings or metal wires in these multiple structure may have a cross sectional dimension which is the same as or different from the dimensions of the other capillary tubings or metal wires according to need.

The above described process of integrating a capillary tubing and a metal wire in any way can be performed continuously by using a capillary tubing of continuous length and a metal wire of also continuous length to give an integrated body of continuous length. The pore of the capillary tubing of the thus obtained integrated body is then filled with a vaporizable substance which should be liquid or in a finely divided particulate form at least during the procedure of filling although it is quite a matter of choice that the capillary tubing is filled with the vaporizable substance prior to the integration thereof with the metal wire. A liquid vaporizable substance is readily introduced into the pore of a capillary tubing when a suitable means of pressurization or suction is provided and a vaporizable substance in particulate form can be introduced into the pore by a pneumatic means. It is further possible to introduce a vaporizable substance which is solid at room temperature into the pore in the form of a melt and solidified in the pore when it has sufficient heat stability. At any rate, a continuous-length integrated body of a capillary tubing and a metal wire is obtained with the vaporizable substance filling the pore of the capillary tubing.

Such a continuous-length body can rarely be used as such so that it is usually cut into desired unit lengths of, for example, at least three times of the outer diameter of the capillary tubing as is mentioned before. When the vaporizable substance contained in the pore of the capillary tubing is liquid at room temperature or at the temperature of use of the inventive sustainedly vapor-releasing body, the body thus obtained by cutting in a unit length suitable for use should be sealed at least at one end of the capillary tubing since otherwise the liquid vaporizable substance cannot be retained in the capillary tubing. It is of course optional that the body is sealed at both ends of the capillary tubing depending on the vaporizability of the vaporizable substance contained therein.

The most convenient and efficient way for sealing one or both ends of the capillary tubing in each of the unit-length bodies is as follows. Thus, the continuous-length body obtained by the integration of the capillary tubing and the metal wire and filled with the vaporizable substance in the pore of the capillary tubing is subjected to heat sealing at portions each in the length of a few millimeters, preferably, with regular intervals to be partitioned into sections of the desired unit lengths and cutting of the thus partitioned body is performed within each of the thus heat-sealed portions or at the closely adjacent position to each of the sealed portions always at the same side of the sealed portion. It is readily understood that cutting within the sealed portions of the continuous-length body gives unit-length bodies each sealed at both ends of the capillary tubing while cutting at the adjacent positions to the sealed portions gives unit-length bodies each sealed only at one end of the capillary tubing.

Figure 6:
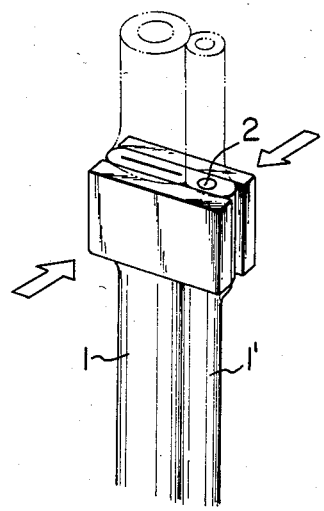
FIG. 6 is a perspective view illustrating the manner of heat sealing at portions of a continuous-length integrated body.
Figure 7:
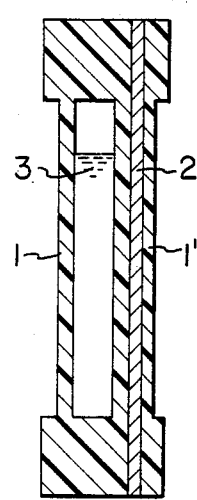
FIG. 7 is an axial cross sectional view of the inventive sustainedly vapor-releasing body sealed at both ends of the capillary tubing.
Figure 8:
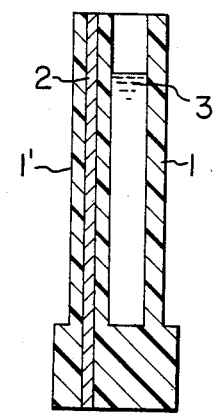
FIG. 8 is an axial cross sectional view of the inventive sustainedly vapor-releasing body sealed at one end of the capillary tubing.

FIG. 6 illustrates the manner in which the heat sealing is effected. The integrated body of the capillary tubing and the metal wire is pressed at the position to be sealed in the radial direction indicated by the arrows between die heads with heating means so that the capillary tubing is collapsed with exclusion of the vaporizable substance and the opposed walls of the capillary tubing are melted together to effect sealing. FIG. 7 is an axial cross sectional view of a unit-length body sealed at both ends of the capillary tubing 1 filled with the vaporizable substance 3 and integrated with the metal wire 2 having a covering layer 1'. The pore of the capillary tubing 1 is not necessarily filled completely with the vaporizable substance 3 but a void space may be left above the vaporizable substance 3 as is shown in FIG. 7. FIG. 8 illustrates a unit-length body sealed only at one end of the capillary tubing 1 by the axial cross sectional view obtained by cutting a continuous-length body with heat-sealed portions at the closely adjacent positions to the heat-sealed portions. In this case, the vapor of the vaporizable substance 3 can effuse from the open end of the capillary tubing 1 in addition to the diffusion-controlled evaporation through the walls of the capillary tubing 1.

In the followings, preparation and application of the inventive sustainedly vapor-releasing bodies are described in further detail by way of examples.

EXAMPLE 1

A capillary tubing of a low-density polyethylene having an inner diameter of 0.8 mm and an outer diameter of 1.6 mm was integrally bonded side-by-side by heat-melting with a BWG #24 iron wire having a 0.3 mm thick covering layer of the same low-density polyethylene as above to give a continuous-length integrated body of about 1000 m long. The pore of the capillary tubing was then filled with a floral type fragrance compound prepared by blending 593 parts by weight of beta-hydroxyphenylethyl alcohol, 309 parts by weight, of benzyl acetate, 33 parts by weight of lily aldehyde, 28 parts by weight of geraniol, 27 parts by weight of linalool, 8 parts by weight of ethylene brassylate and 2 parts by weight of cis-3-hexenyl tiglate. The thus obtained continuous-length body filled with the fragrance compound was heat-sealed at every 30 cm, each sealed portion having a length of a few millimeters, and then cut within the sealed portions to give about 3300 pieces of the unit-length bodies each sealed at both ends of the capillary tubing. The fragrance was noticeably emitted through the walls of the polyethylene capillary tubing.

The fragrance-emitting body of about 30 cm length was used as the stalk of an artificial flower after coloring in green and by attaching plastic-made leaves and flowers. By virtue of the good shape-retainability of the body, any desired shapeliness could be imparted to the stalk of the artificial flower readily by hand so that the artificial flower could have an appearance of a living flower. In addition, the artificial flower could be held upright even without a prop to exhibit very good decorative effect when arranged in a room into which the floral-type fragrance contained in the stalk was continuously emitted over a period of 3 months or longer.

For comparison, the same polyethylene capillary tubing filled with the frangrance compound but without integration with the metal wire was used in the same purpose as above only to find that no satisfactory artificial flowers could be prepared due to the excessive flexibility of the stalks.

EXAMPLE 2

A capillary tubing of a high-density polyethylene having an inner diameter of 0.5 mm and an outer diameter of 1.0 mm was integrally bonded side-by-side by heat melting with a BWG #24 iron wire having a 0.3 mm thick covering layer of the same high-density polyethylene as above to give a continuous-length integrated body of about 2000 m long. The pore of the capillary tubing was then filled with a citrus floral-type fragrance compound prepared by blending 659 parts by weight of dextro-limonene, 158 parts by weight of beta-hydroxyphenylethyl alcohol, 76 parts by weight of lily aldehyde, 76 parts by weight of heliotropin and 31 parts by weight of vanillin. Heat-sealing and cutting of the thus obtained integrated continous-length body filled with the fragrance compound were performed in the same manner as in Example 1 to give about 6600 pieces of the unit-length bodies emitting the fragrance contained therein and each having a length of 30 cm and sealed at both ends of the capillary tubing.

Artificial flowers were prepared by use of these fragrance-containing integrated bodies as the stalks. When several of these artificial flowers were placed in a lavatory, the offensive odor there was greatly mitigated by virtue of the odor-masking power of the citrus floral-type fragrance emitted over a period of about 2 months. Meanwhile, no artificial flowers of good shapeliness could be prepared, by use of the same polyethylene capillary tubing but without integration with the iron wire.

EXAMPLE 3

A capillary tubing of a low-density polyethylene having an inner diameter of 0.8 mm and an outer diameter of 1.3 mm was integrally bonded side-by-side by heat melting with a BWG #22 iron wire having a 0.25 mm thick covering layer of the same low-density polyethylene as above to give a continuous-length integrated body of about 10,000 m long. The pore of the capillary tubing was then filled with a liquid mixture prepared by blending 500 parts by weight of cis-11-dodecenyl acetate and 500 parts by weight of cis-9-tetradecenyl acetate known as the main components of the sex pheromones of tea tortrix and smaller tea tortrix with admixture of 0.05 part by weight of butylated hydroxyanisole as an anti-oxidant stabilizer.

Heat sealing and cutting of the thus prepared pheromone-containing integrated body were performed at every 10 cm in the same manner as in Example 1 to give about 100,000 pieces of the unit-length bodies each sealed at both ends of the capillary tubing.

The shape-retainability of the pheromone-containing integrated bodies was evaluated and compared with the results of the same polyethylene capillary tubing filled with the same pheromone mixture but without integration with the iron wire in the following manner. Thus, the integrated body or the comparative single body of the capillary tubing was put on to a glass rod of 8 mm diameter perpendicularly and bent by 180° or 360° around the glass rod while being perpendicularly pressed against the glass rod. After keeping the body for 0.5 second in this compulsorily bent disposition, the outer bending force was released with immediate removal of the glass rod and the bent body was kept free for a while. The angle formed between two legs of the bent body was measured at moments of 5 seconds, 5 minutes, 12 hours and 24 hours after the release of the outer force and the restoration of the angle from 180° or 360° was calculated to give the results shown in Table 1 below.

TABLE 1

| The body bent at an angle of | Time of keeping with released outer force | Angle restoration | |
|---|---|---|---|
| | | Integrated body | single body |
| 180° | 5 seconds | 6° | 160° |
| | 5 minutes | 8° | 170° |
| | 12 hours | 10° | 180° |
| | 24 hours | 10° | 180° |
| 360° | 5 seconds | 22° | 335° |
| | 5 minutes | 28° | 350° |
| | 12 hours | 30° | 360° |
| | 24 hours | 30° | 360° |

As is shown in the table, the restoration of the bending angle was 90% or more in the case of the single bodies without integration with the iron wire at a moment of 5 seconds, or rather immediately in a practical sense, after the release of the outer bending force irrespective of the angle of the compulsory bending while the angle restoration in the integrated bodies levelled off at about 12 hours after the release of the outer bending force with maximum restoration of only 5 to 8% retaining the complete loop formed by the 360° bending even after 24 hours.

The handling efficiency of these pheromone-containing vapor-releasing bodies was eveluated in an actual field test in a tea garden for the control of the above mentioned pests of tea plants by hanging the vapor-releasing bodies on the sprigs of the tea plant located near the top of the plant at about the same height as the flying height of the pests in order to obtain best disordering effect on the mating communication of them.

The vapor-releasing body integrated with the iron wire could be hung with very high efficiency by merely bonding by 360° to form a loop or by a single-turn winding at and around a spring of the tea plant taking only 0.3 to 0.5 second for each of the bodies. All of the thus hanging bodies were found remaining on the sprigs after 3 months during which period considerably strong wind blew several times and the pheromones contained therein had been almost completely evaporated through the walls of the capillary tubings.

On the other hand, attempts were made to hang the single bodies of the capillary tubing without integration with an iron wire on the sprigs of the tea plants in a similar manner without success since the bodies once wound around the sprigs became readily unwounded and fell on the ground due to the poor shape-retainability thereof so that the pheromones could exhibit the effect no longer. In order to provide a hanging means somehow, a wire was fastened to each of the bodies at one end thereof by handworks and the vapor-releasing body was hung on the sprig of the tea plant utilizing this wire as the hanging hook. In this case, the labor required for hanging of 100,000 pieces of the vapor-releasing bodies was about 140 man.hour or about 5 seconds for each on an average to be far less efficient than in the case of the integrated vapor-releasing bodies.

What is claimed is:

1. A sustainedly vapor-releasing integrated body having excellent shape-retainability which comprises
    (a) a capillary tubing sealed at both ends and having flexibility made of a polymeric material,
    (b) a metal wire having plastic deformability to retain a deformed configuration and integrated with the capillary tubing in a side-by-side manner along the longitudinal direction thereof, and (c) a vaporizable substance filling the pore of the capillary tubing, which is capable of vaporizing through the walls of the capillary tubing and exhibiting an activity in the vapor phase.

2. The sustainedly vapor-releasing integrated body as claimed in claim 1 wherein the metal wire has a covering layer made of a polymeric material.

3. The sustainedly vapor-releasing integrated body as claimed in claim 2 wherein the covering layer on the metal wire is made of the same polymeric material as the polymeric material of which the capillary tubing is made.

4. The sustainedly vapor-releasing integrated body as claimed in claim 1 wherein the metal wire is integrated with the capillary tubing by bonding with an adhesive agent.

5. The sustainedly vapor-releasing integrated body as claimed in claim 1 or claim 2 wherein the metal wire with or without a covering layer is integrated with the capillary tubing by melting the polymeric material.

6. The sustainedly vapor-releasing integrated body as claimed in claim 1 wherein the metal wire and the capillary tubing are integrated by intertwisting.

7. The sustainedly vapor-releasing integrated body as claimed in claim 1 wherein the metal wire integrated with the capillary tubing has a length substantially equal to the length of the capillary tubing with the end surfaces being flush.

8. The sustainedly vapor-releasing integrated body as claimed in claim 1 wherein the metal wire has a sufficiently large cross section such that the integrated body, when deformed by the application of an outer force, can retain the deformed configuration when the outer force is released resisting the resilience of the capillary tubing.

9. The sustainedly vapor-releasing integrated body as claimed in claim 1 wherein the metal wire is made of a metal selected from the group consisting of aluminum, copper and iron.

10. A method for the preparation of a sustainedly vapor-releasing integrated body comprising
(a) a capillary tubing having flexibility made of a polymeric material sealed at least at one end thereof,
(b) a metal wire having plastic deformability to retain a deformed configuration and integrated with the capillary tubing in a side-by-side manner along the longitudinal direction thereof, and
(c) a vaporizable substance filling the pore of the capillary tubing, which is capable of vaporizing through the walls of the capillary tubing and exhibiting an activity in the vapor phase, which comprises the steps of
  (i) integrating side-by-side a capillary tubing and the metal wire each in a continuous length to form a continuous-length integrated body,
  (ii) filling the pore of the capillary tubing with the vaporizable substance,
  (iii) heat-sealing the capillary tubing filled with the vaporizable substance at portions with intervals to partition the pore of the capillary tubing into sections and
  (iv) cutting the integrated body into unit-length bodies at positions within the sealed portions or at positions closely adjacent to the sealed portions always at the same side of the sealed portion.

* * * * *